(12) United States Patent
Bencini

(10) Patent No.: US 6,925,318 B2
(45) Date of Patent: Aug. 2, 2005

(54) MEDICAL PROBE WITH VARIABLE TIP LENGTH AND SHAPE

(75) Inventor: Robert F. Bencini, Sunnyvale, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 90 days.

(21) Appl. No.: 10/173,469

(22) Filed: Jun. 14, 2002

(65) Prior Publication Data

US 2003/0233037 A1 Dec. 18, 2003

(51) Int. Cl.[7] .......................... A61B 5/042; A61B 18/14
(52) U.S. Cl. ......................... 600/374; 606/41; 607/122
(58) Field of Search ........................... 600/374; 606/41, 606/45–50; 607/122

(56) References Cited

U.S. PATENT DOCUMENTS

| | | | | |
|---|---|---|---|---|
| 3,754,555 A | * | 8/1973 | Schmitt | 607/128 |
| 3,814,104 A | * | 6/1974 | Irnich et al. | 607/128 |
| 4,664,120 A | * | 5/1987 | Hess | 600/374 |
| 4,900,303 A | * | 2/1990 | Lemelson | 604/514 |
| 5,085,659 A | * | 2/1992 | Rydell | 606/47 |
| 5,234,429 A | * | 8/1993 | Goldhaber | 606/45 |
| 5,921,982 A | * | 7/1999 | Lesh et al. | 606/41 |
| 6,322,586 B1 | | 11/2001 | Monroe et al. | |
| 6,325,790 B1 | | 12/2001 | Trotta | |
| 6,374,476 B1 | | 4/2002 | Ponzi et al. | |
| 2002/0049424 A1 | | 4/2002 | Fulford | |
| 2002/0052641 A1 | | 5/2002 | Monroe | |

\* cited by examiner

*Primary Examiner*—Lee S. Cohen
(74) *Attorney, Agent, or Firm*—Bingham McCutchen LLP

(57) ABSTRACT

A tip assembly that can be varied in length and/or shape is coupled to an elongated sheath to form a medical probe, such as a catheter or surgical probe. For example, the medical probe can be an electrophysiology (EP) catheter that that can be used to map the electrical activity of target tissue and ablate the target tissue when medically indicated. In one embodiment, the tip assembly has a tip and a sleeve configured such that the tip can be longitudinally extended and retracted in response to longitudinal forces applied by an actuator. In another embodiment, the tip extends and retracts, on threads, relative to the sleeve in response to rotational forces applied by an actuator. In still another embodiment, the tip assembly has a distal tip, a proximal section and an expandable-compressible assembly between the tip and proximal section. The expandable-compressible assembly is configured to be longitudinally compressed and expanded, expanding radially outward when compressed, and compressing radially inward when longitudinally expanded, thereby altering the tip assembly shape.

7 Claims, 2 Drawing Sheets

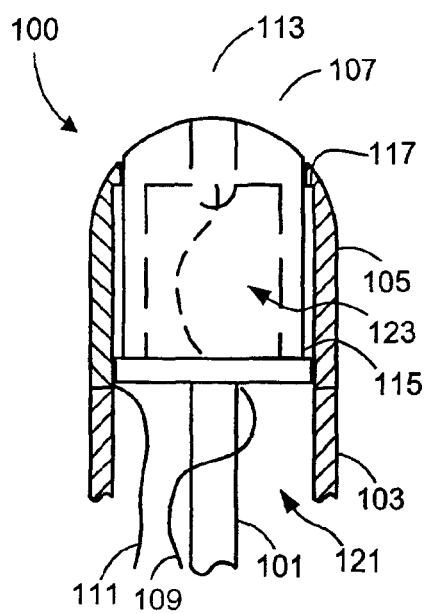
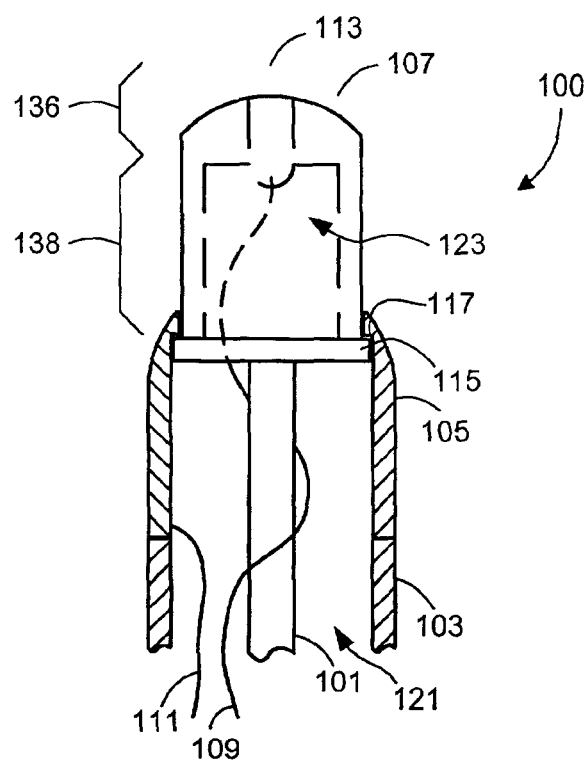
FIG. 1A
FIG. 1B
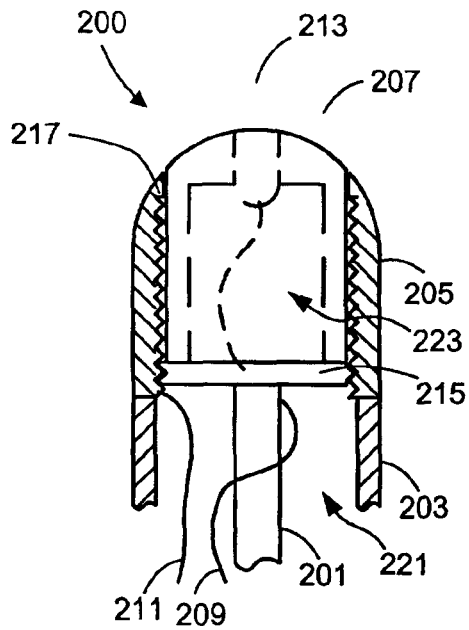
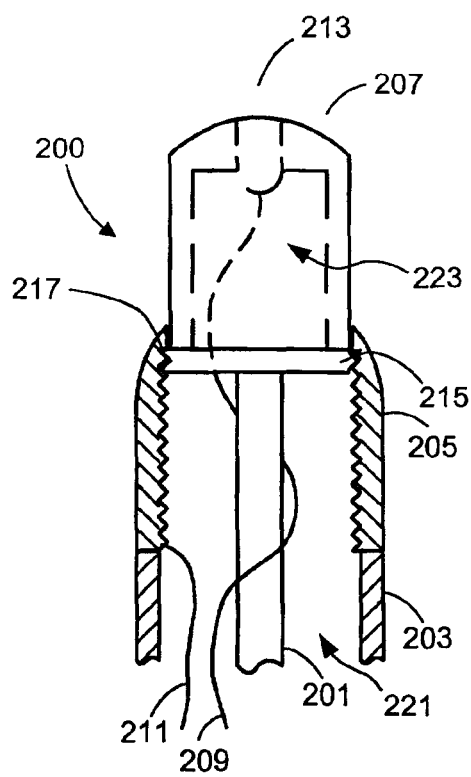
FIG. 2A
FIG. 2B

MEDICAL PROBE WITH VARIABLE TIP LENGTH AND SHAPE

FIELD OF INVENTION

The invention relates generally to medical devices, and more particularly, to invasive medical probes and the tips associated with them.

BACKGROUND

Medical probes are widely used in the medical arts. For example, medical probes in the form of catheters are sometimes inserted into a patient's body during valve mapping and ablation procedures of the patient's heart. Catheters used for such procedures are typically comprised of metallic electrode tips of various shapes and sizes. Selection of the proper size by the physician depends largely upon the patient's anatomy, the procedure and physician preference.

Catheters of present manufacture are typically made with a platinum tip of a fixed length, ranging in length from about 4 mm, 5 mm, 6 mm up to about 10 mm. They are generally manufactured with a 7 French or 8 French diameter. The choice of overall length depends primarily on the length of the target tissue to be ablated. Present catheter tip shapes are hemispherical at the distal end, transitioning into a cylindrical portion proximal to the attached sheath. The hemispherical distal end is an aid to threading the catheter through blood vessels without interference, while the cylindrical section makes up the balance of the overall length.

After insertion of a platinum tipped catheter, mapping results may indicate the need for a larger (or smaller) platinum tip. Having to exchange catheters extends the time required to complete the procedure and places the patient at greater risk. Further, the 1 mm incremental sizing of the present catheters does not allow for fine control over the length of the ablated tissue. In addition, should the shape of the target tissue be highly convoluted, the cylindrical portion of the tip may not make uniform contact, causing the ablation to progress non-uniformly, making it difficult for the physician to achieve the desired result.

SUMMARY OF THE INVENTION

In one aspect, a medical probe is provided with a distal tip that can be varied in length and/or shape. In one embodiment, the medical probe, which can be, e.g., a catheter or surgical probe, comprises an elongated sheath, and a tip assembly mounted to its distal end. By way of non-limiting example, the tip assembly can be electrically conductive and function as a mapping and/or ablation electrode, in which case, one or more radio frequency/mapping wires can be electrically coupled thereto. The tip assembly is configured, such that it can alternately be placed into a longitudinally retracted or extended configuration.

In one embodiment, the tip assembly includes a sleeve and a tip configured to be alternately displaced distally and proximally relative to the sleeve. By this configuration, the length of the tip assembly can be alternately lengthened or shortened. By way of non-limiting example, the tip may be displaced relative to the sleeve in the presence of, e.g., a longitudinal mechanical force, or if the tip and sleeve are in a threaded arrangement, a rotational mechanical force. The medical probe can include an actuator, preferably in the form of a control wire to deliver these mechanical forces. Other types of actuators, such as fluid pressure actuators or wireless actuators, are also contemplated.

In another embodiment, the probe may comprise a mechanical stop to limit distal movement of the tip relative to the sleeve for the purpose of, e.g., maintaining the structural and operational integrity of the tip assembly. This mechanical stop can include, e.g., a flange disposed on the outside of the tip, and a shoulder disposed on the inside of the sleeve. In this case, the shoulder interferes with the flange to limit the distal movement of the tip. The mechanical stop can also be applied to the actuator, e.g. by limiting the travel of the control wire. Although such a control wire stop can be applied at any location along its length, it is advantageously applied to the control wire at the proximal end of the medical probe.

In accordance with another aspect, embodiments of the tip assembly include a distal tip, a proximal section, e.g., a ring, and an expandable-compressible assembly between the tip and the proximal section. The expandable-compressible assembly is configured to be longitudinally compressed and expanded when the distal tip is displaced distally and proximally relative to the proximal section. In this manner, the length of the tip assembly can be alternately lengthened or shortened. By way of non-limiting example, the tip may be displaced relative to the proximal section in the presence of, e.g., a longitudinal mechanical force. The medical probe can include an actuator such as a control wire to deliver these mechanical forces.

In some embodiments, the general shape of the tip assembly can be altered. For example, the expandable-compressible assembly may expand radially outward when longitudinally compressed, and compress radially inward when longitudinally expanded. To effect the change in shape, the expandable-compressible assembly can be formed from a flexible and expandable material such as surgical rubber, or a collection of links configured for such purpose. In the preferred embodiment, the expandable-compressible assembly comprises a toggle assembly that includes a first link hinged to the distal tip and a second link hinged to the proximal section of the elongated sheath.

BRIEF DESCRIPTION OF THE DRAWINGS

The drawings illustrate the design and utility of embodiments of the invention, in which similar elements are referred to by common reference numerals. The illustrative embodiments of the invention are not to be considered limiting of its scope.

FIG. 1A is a partial cutaway side view of a first embodiment of a variable tip length tip assembly particularly shown in its collapsed (minimum length) configuration;

FIG. 1B is a partial cutaway side view of the variable tip length assembly of FIG. 1A particularly shown in its extended (maximum length) configuration;

FIG. 2A is a partial cutaway side view of a second embodiment of a variable tip length tip assembly particularly shown in its collapsed (minimum length) configuration;

FIG. 2B is a partial cutaway side view of the variable tip length assembly of FIG. 2A particularly shown in its extended (maximum length) configuration;

DETAILED DESCRIPTION OF THE ILLUSTRATED EMBODIMENTS

Figure 2C:
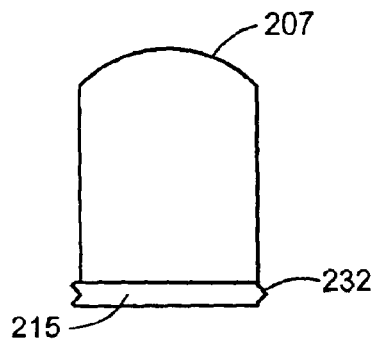
FIG. 2C is a side view of the tip component used in the assembly of FIGS. 2A and 2B.

FIGS. 1A and 1B depict a variable length tip assembly 100 constructed in accordance with one embodiment of the invention. FIG. 1A depicts the tip assembly 100 in a minimum length, retracted configuration. FIG. 1B depicts the tip assembly 100 in a maximum length, extended configuration.

The tip assembly 100 is coupled to an elongated medical probe sheath to form a medical probe. In the illustrated embodiment, the meical probe sheath is an elongated catheter sheath 103, and the medical probe is an electrophysiology (EP) catheter. The tip assembly 100 has a sleeve 105 and a tip 107 that longitudinally moves within the sleeve 105, and a thermistor 113.

A RF/mapping wire 111, and thermistor cable 109 extend from the tip assembly 100 to a distal portion of the elongated catheter sheath 103, each contained in a lumens 121 and 123 of the sheath 103 and tip assembly 100. An actuator, preferably a control wire 101 is operatively coupled to the tip 107 causing the tip 107 to move relative to the sleeve 105. A mechanical stop 115 limits the travel of the tip 107.

The sleeve 105 and tip 107 are electrically conductive in order to electrically couple the target tissue to the tip assembly 100. The cores of the sleeve 105 and tip 107 can be fabricated from an electrically conductive material (such as platinum, copper, or stainless steel), or an insulating material (such as plastic). If the cores of the sleeve 105 and the tip 107 are fabricated from an insulating material, the outer surfaces of the sleeve 105 and the tip 107 are preferably plated or coated with an acceptable biocompatible conductive layer, such as, e.g., platinum or gold, in order to improve or maintain electrical coupling with the target tissue. Portions of the inner surfaces may also be plated or coated with a conductive layer in order to improve or maintain conductivity between the sleeve 105 and tip 107 and provide contacts for external electrical circuitry. If the cores of the sleeve 105 and tip 107 are fabricated from electrically conductive material, an optional coating or plating of inner or outer surfaces may be advantageously applied to improve the electrical characteristics.

The tip 107 has a shank section 138, which has a uniform cross section and a tip section 136, which is generally a rounded convex shape to help guide the catheter during insertion and prevent the tip section from puncturing, snagging or damaging the surrounding tissue. The sleeve 105 is slidably coupled to the tip 107, allowing telescoping motion of the tip assembly 100. The lumen 123 of the tip assembly 100 is in communication with the lumen 121 of the sheath 103, allowing the control wire 101, RF/mapping wire 111 and thermistor cable 109 to pass from the tip assembly 100 through the sheath 103 without interference.

Control wire 101 is operatively coupled to the tip 107 such that reciprocating mechanical forces applied to the distal end of the control wire 101 cause the tip 107 to retract into the sleeve 105 (FIG. 1A) or extend from the sleeve 105 (FIG. 1B). The cross sections of the telescoping surfaces of the tip 107 and sleeve 105 are uniform and preferably circular; however a skilled practitioner in the art will appreciate that any shape which allows telescoping motion may be used advantageously depending, in part, on anatomy and the target tissue. By way of non-limiting example, rectangular, oval, and elliptical cross-sections may be used.

It is preferred that the tip 107 remains captured by the sleeve 105. If the tip 107 were allowed to extend too far, misalignment and interference of the tip 107 with the sleeve 105 could make it difficult or impossible to retract the tip 107 into the sleeve 105. For example, this can happen if the tip 107 is allowed to extend beyond the point where the telescoping surfaces of the tip 107 and sleeve 105 would lose contact, and can also happen as this point is approached. As the overlapping section of the telescoping surfaces approaches a small fraction of the tip 107 width, the tip 107 can tilt and jam in the sleeve 105. For these reasons, it is important to prevent the tip 107 from extending too far.

As such, the mechanical stop 115 is used to limit the travel of the tip 107 with respect to the sleeve 105. Numerous types of mechanical stops can be used, which are well known in the art. In the preferred embodiment depicted in FIGS. 1A and 1B, the stop 115 is applied to the sleeve 105 and tip 107 with interfering flange 115 and shoulder 117, the flange 115 applied to the base of the tip 107 and the shoulder 117 applied to the mouth of the sleeve 105. Optionally or alternatively, a mechanical stop can be applied to a manipulator handle (not shown) at the distal end of the sheath 103 to limit the travel of the control wire 101.

The RF/mapping wire 111 is electrically coupled to the tip assembly 100 on its proximal end, and passes through the lumen 123 of the tip assembly 100 and the lumen 121 of the sheath 103. The RF/mapping wire 111 can be electrically coupled to the tip 107, the sleeve 105, or both. During an EP catheterization procedure, the tip assembly 100 is positioned in close contact with the target tissue for mapping of electrical activity. These mapping signals are carried by the RF/mapping wire 111 to its distal end where the electrical signals are detected and used for diagnosis and formulation of a treatment strategy.

During ablation procedures, high power RF energy applied to the distal end of the RF/mapping wire 111 is carried to the tip assembly 100 where the energy is subsequently delivered to the target tissue. This RF energy causes the tissue in close proximity to the tip assembly 100 to heat to a sufficiently high temperature that a portion of the tissue is ablated.

Controlling the amount of RF energy delivered to the target tissue is important to achieving the desired clinical results. Too little energy and the temperature rise in the target tissue will be insufficient to cause ablation. Too much energy will cause ablation to affect too much tissue. The temperature of the tissue is a primary indication of the amount of RF energy delivered to it and is therefore quite useful in controlling the amount. The thermistor 113 is used for the purpose of measuring the temperature of the tip assembly 100 and consequently the tissue in close proximity.

The thermistor 113 is disposed in the tip 107 in a way that facilitates temperature measurement of the tissue in close proximity to the tip assembly 100. A portion of the thermistor 113 may form a portion of the tip surface 107 or may be positioned slightly below the surface. The thermistor 113 is preferably disposed on or near the tip of the tip 107. The thermistor cable 109 may be comprised of one or more electrical conductors, the conductor(s) providing electrical power and stimulus signals to the thermistor 113, and bringing temperature measurement signals from the thermistor 113 to detection electronics.

FIGS. 2A and 2B depict a variable length tip assembly 200 constructed in accordance with another embodiment of the invention. FIG. 2A depicts the tip assembly 200 in a minimum length, retracted configuration. FIG. 2B depicts the tip assembly 200 in a maximum length, extended configuration.

This tip assembly 200 is similar to the previously described tip assembly 100, except that the tip advances through the sleeve on threads. The tip assembly 200 is coupled to an elongated medical probe sheath to form a medical probe. Like with previous illustrated embodiment, the medical probe sheath is an elongated catheter sheath 203, and the medical probe is an electro-physiology (EP) catheter. The tip assembly 200 has a sleeve 205, a rotating tip 207, and a thermistor 213. A control wire 201, a RF/mapping wire 211, and a thermistor cable 209 extend from the tip assembly 200 to a distal portion of the elongated catheter sheath 203, each contained in a lumens 221 and 223 of the sheath 203 and tip assembly 200. A mechanical stop, including a flange 215 and shoulder 215, limits the travel of the tip 207.

Similar to the first embodiment, the sleeve 205 and tip 207 can be fabricated from an electrically conductive material or an insulating material, with materials or outer surfaces preferably of platinum or gold. Portions of the inner surfaces may also be plated or coated with a conductive layer to improve conductivity between the sleeve 205 and tip 207 and provide contacts for external electrical circuitry.

Figure 2D:
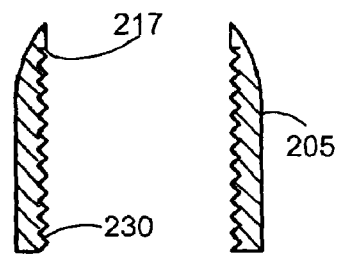
FIG. 2D is a cutaway view of the sleeve component used in the assembly illustrated in FIGS. 2A and 2B.

The sleeve 205 has internal threads 230 (best shown in FIG. 2D), which engage external threads 232 applied to a flange 215 on the base of the tip 207 (best shown in FIG. 2C). Control wire 201 is operatively coupled to the tip 207 such that rotational mechanical forces applied to the distal end of the control wire 201 cause the tip 207 to retract into the sleeve 205 (FIG. 2A) or extend from the sleeve 205 (FIG. 2B) by advancing along the threads 230 and 232 as the tip 207 rotates. The lumen 223 of the tip assembly 200 is in communication with the lumen 221 of the sheath 203, allowing the control wire 201, RF/mapping wire 211 and thermistor cable 209 to pass from the tip assembly 200 through the sheath 203 without interference.

It is important to ensure that all exposed surfaces of the EP catheter are smooth, to reduce the risk that the catheter could damage or cut surrounding tissues. If the tip 207 were allowed to extend too far, the sharp edges of the threads on the base would be exposed, posing a safety risk for the patient. For these reasons, it is important to prevent the tip 207 from extending too far.

As such, a mechanical stop is used to limit the travel of the tip 207 with respect to the sleeve 205. In the preferred embodiment depicted in FIGS. 2A, 2B and 2D, the stop has an interfering flange 215, which carries the external threads 232, and a shoulder 217 applied to the mouth of the sleeve 205. Note that the shoulder 217 can be formed by simply terminating the internal threads 230 before the mouth of the sleeve 205. Alternative or optionally, a mechanical stop can be applied to the manipulator handle (not shown) at the distal end of the sheath 103, by limiting the revolutions of the control wire 201.

The RF/mapping wire 211 is electrically coupled to the tip assembly 200, and the thermistor 213 is associated with the tip 207 in the same manner previously described with respect to the tip assembly 100. Sufficient slack in the thermistor cable 209 is provided so that as the tip 207 rotates from its retracted position to its extended position, the cable 209 wraps around control wire 201 without interference or tension. Similarly, if the RF/mapping wire 211 is coupled to the rotating tip 207, sufficient slack is provided so that as the tip 207 rotates from its retracted position to its extended position, the RF/mapping wire 211 wraps around control wire 201 without interference or tension.

Figure 3A:
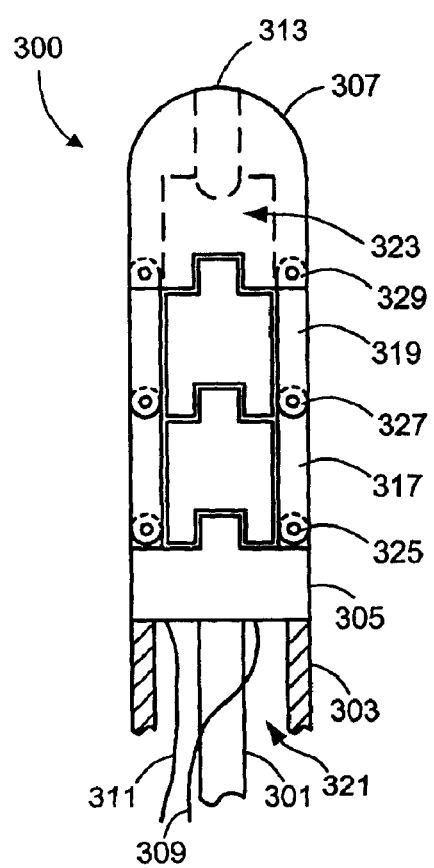
FIG. 3A is an illustration of a third embodiment of a variable tip length/shape assembly particularly shown in its extended (maximum length) configuration.
Figure 3B:
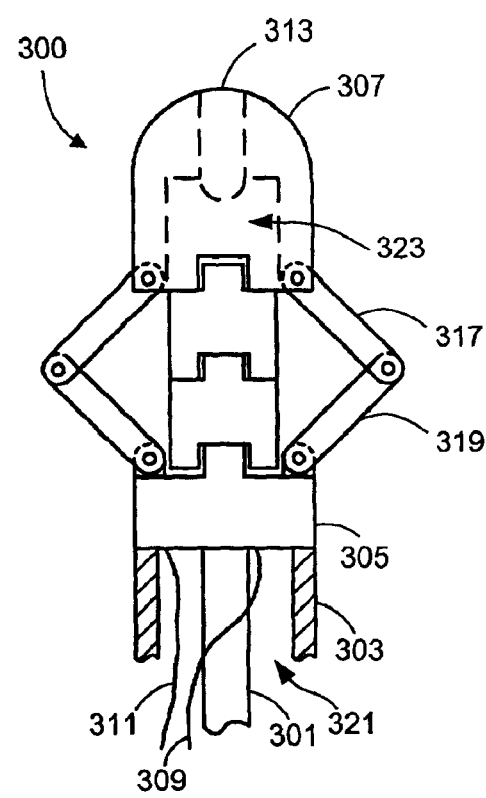
FIG. 3B is an illustration of the third embodiment of the variable tip length assembly particularly shown in its collapsed (minimum length) configuration.

FIGS. 3A and 3B depict a variable length/shape tip assembly 300 constructed in accordance with yet another embodiment of the invention. FIG. 3A depicts the tip assembly 300 in a maximum length and minimum width, extended configuration. FIG. 3B depicts the tip assembly 300 in a minimum length and maximum width retracted configuration.

The tip assembly 300 is coupled to an elongated medical probe sheath to form a medical probe. Like with previous illustrated embodiments, the medical probe sheath is an elongated catheter sheath 303, and the medical probe is an electro-physiology (EP) catheter. The tip assembly 300 has a ring 305, a tip 307, a thermistor 313, and an intermediate assembly that expands when compressed. In the preferred embodiment, this expandable-compressible assembly is implemented with first and second toggle links 317, 319. A control wire 301, an RF/mapping wire 311, and a thermistor cable 309 extend from the tip assembly 300 to a distal portion of the elongated catheter sheath 303, each contained in lumens 321 and 323 of the sheath 303 and tip assembly 300.

The cores of the ring 305, tip 307, and toggle links 317,319 can be fabricated from an electrically conductive material (such as copper or stainless steel), or an insulating material (such as plastic). If the cores of these components are fabricated from an insulating material, their outer surfaces are preferably plated or coated with an acceptable biocompatible conductive layer, such as, e.g., platinum or gold, in order to improve or maintain electrical coupling with the target tissue. Portions of their inner surfaces may also be plated or coated with a conductive layer in order to improve or maintain conductivity between the components and provide contacts for external electrical circuitry. If the cores of these components are fabricated from electrically conductive material, an optional coating or plating of inner or outer surfaces may be advantageously applied to improve the electrical characteristics.

The tip 307 is mechanically coupled to the ring 305 using the toggle links 317,319, which are coupled thereto with hinges. In particular, toggle links 317 and 319 are coupled to each other at a central point by a hinge 327. Further, the proximal end of the first link 317 is coupled to the ring 305 with a hinge 325, and the distal end of the second link 319 is coupled to the tip 307 with a hinge 329.

Control wire 301 is operatively coupled to the tip 307, such that reciprocating mechanical forces applied to the distal end of the control wire 301 cause the tip 307 to extend (FIG. 3A) or retract (FIG. 3B). In the retracted configuration illustrated in FIG. 3B, the toggle links 317 and 319 are compressed and flare outward, thereby increasing the effective diameter of the tip assembly 300. In the extended configuration illustrated in FIG. 3A, the toggle links 317 and 319 are in tension and are drawn inward, close to the control wire 301, thereby reducing the effective diameter of the tip assembly 300.

The inside of the tip assembly 300 is in communication with the lumen 321 of the sheath 303, allowing the control wire 301, RF/mapping wire 311 and thermistor cable 309 to pass from the tip assembly 300 through the sheath 303 without interference.

The RF/mapping wire 311 functions and is electrically coupled to the tip assembly 300 in the same manner previously described with respect to the tip assembly 100. The thermistor 313 functions and is associated with the tip 307 in the same manner as the thermistor 113 is associated with the tip 107 of the previously described tip assembly 100.

Although particular embodiments of the invention have been shown and described, it will be understood that the invention is not limited to the illustrated embodiments and it will be apparent to those skilled in the art that various changes and modifications may be made without departing from the scope of the invention. Thus, the invention is only to be limited by the appended claims and their equivalents.

What is claimed:

1. A medical probe, comprising:

an elongated sheath;

a tip assembly mounted to the distal end of the sheath, the tip assembly having a sleeve and a tip, the tip configured to be alternately displaced distally and proximally relative to the sleeve, wherein the tip assembly and the tip have smooth exterior surfaces;

an actuator operatively coupled to displace the tip relative to the sleeve, the actuator being configured to displace the tip out of the sleeve and retract the tip into the sleeve; and a mechanical stop to limit distal movement of the tip relative to the sleeve, wherein the mechanical stop comprises a flange disposed on the outside of the tip, and a shoulder disposed on the inside of the sleeve.

2. The probe of claim 1, wherein the tip is displaced relative to the sleeve in the presence of a longitudinal mechanical force.

3. The probe of claim 1, wherein the actuator is a control wire operatively coupled to the tip to displace the tip relative to the sleeve.

4. The probe of claim 1, further comprising a radio frequency/mapping wire connected to the probe tip assembly.

5. The probe of claim 1, wherein the tip is a generally round tip and the sleeve is a generally cylindrical shank.

6. The probe of claim 1, wherein the elongated sheath is a catheter sheath.

7. The probe of claim 1, wherein the tip assembly is composed of an electrically conductive material.

* * * * *

UNITED STATES PATENT AND TRADEMARK OFFICE
CERTIFICATE OF CORRECTION

PATENT NO. : 6,925,318 B2
DATED : August 2, 2005
INVENTOR(S) : Robert F. Bencini It is certified that error appears in the above-identified patent and that said Letters Patent is hereby corrected as shown below:

Column 6,
Line 4, immediately after "width" insert -- $_1$ --.

Signed and Sealed this

Twentieth Day of December, 2005

JON W. DUDAS
*Director of the United States Patent and Trademark Office*